(12) United States Patent
Morton et al.

(10) Patent No.: US 8,929,509 B2
(45) Date of Patent: *Jan. 6, 2015

(54) FOUR-SIDED IMAGING SYSTEM AND METHOD FOR DETECTION OF CONTRABAND

(71) Applicant: Rapiscan Systems, Inc., Torrance, CA (US)

(72) Inventors: Edward James Morton, Guildford (GB); Andreas F. Kotowski, Rancho Palos Verdes, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/864,440

(22) Filed: Apr. 17, 2013

(65) Prior Publication Data

US 2014/0177793 A1 Jun. 26, 2014

Related U.S. Application Data

(63) Continuation of application No. 12/834,890, filed on Jul. 12, 2010, now Pat. No. 8,503,605, which is a
(Continued)

(51) Int. Cl.
*G01N 23/04* (2006.01)
*G01V 5/00* (2006.01)
*G01N 23/203* (2006.01)

(52) U.S. Cl.
CPC .............. *G01N 23/04* (2013.01); *G01V 5/0016* (2013.01); *G01V 5/0025* (2013.01); *G01V 5/0041* (2013.01); *G01V 5/0066* (2013.01); *G01N 23/203* (2013.01)
USPC .......................................................... 378/57

(58) Field of Classification Search
USPC .................... 378/57, 62, 145, 153, 160, 98.8
See application file for complete search history.

(56) References Cited

U.S. PATENT DOCUMENTS

| 2,831,123 A | 4/1958 | Daly |
| 3,766,387 A | 10/1973 | Heffan et al. |

(Continued)

FOREIGN PATENT DOCUMENTS

| EP | 0261984 A2 | 3/1988 |
| EP | 0864884 A2 | 9/1998 |

(Continued)

OTHER PUBLICATIONS

International Search Report and Written Opinion for PCT/US2010/041757 filed on Jul. 13, 2010.
(Continued)

*Primary Examiner* — Irakli Kiknadze
(74) *Attorney, Agent, or Firm* — Novel IP

(57) ABSTRACT

The present invention provides a four-sided scanning system for vehicles that uses a combination of backscatter and transmission based X-ray imaging to achieve material discrimination. In one embodiment, the system is designed as a mobile, drive-through system, which can be folded and stowed in a truck and can be conveniently deployed at any place when required.

21 Claims, 10 Drawing Sheets

Related U.S. Application Data continuation-in-part of application No. 12/784,630, filed on May 21, 2010, now Pat. No. 8,275,091, said application No. 12/834,890 is a continuation-in-part of application No. 12/753,976, filed on Apr. 5, 2010, now Pat. No. 7,995,705, which is a continuation-in-part of application No. 12/349,534, filed on Jan. 7, 2009, now Pat. No. 7,720,195, which is a continuation of application No. 10/939,986, filed on Sep. 13, 2004, now Pat. No. 7,486,768, which is a continuation-in-part of application No. 10/915,687, filed on Aug. 9, 2004, now Pat. No. 7,322,745, which is a continuation-in-part of application No. 10/201,543, filed on Jul. 23, 2002, now Pat. No. 6,843,599, said application No. 12/834,890 is a continuation-in-part of application No. 12/396,568, filed on Mar. 3, 2009, now Pat. No. 7,817,776, which is a continuation-in-part of application No. 11/948,814, filed on Nov. 30, 2007, now Pat. No. 7,517,149, which is a continuation of application No. 10/915,687, filed on Aug. 9, 2004, now Pat. No. 7,322,745, said application No. 12/834,890 is a continuation-in-part of application No. 12/395,760, filed on Mar. 2, 2009, now Pat. No. 7,876,880, which is a continuation-in-part of application No. 12/051,910, filed on Mar. 20, 2008, now Pat. No. 7,519,148, which is a continuation-in-part of application No. 11/622,560, filed on Jan. 12, 2007, now Pat. No. 7,369,463, said application No. 12/834,890 is a continuation-in-part of application No. 12/339,591, filed on Dec. 19, 2008, now Pat. No. 7,963,695, said application No. 12/834,890 is a continuation-in-part of application No. 12/263,160, filed on Oct. 31, 2008, now Pat. No. 7,783,004, said application No. 12/834,890 is a continuation-in-part of application No. 12/675,471, filed as application No. PCT/GB2008/002897 on Aug. 29, 2008, now abandoned.

(60) Provisional application No. 61/180,471, filed on May 22, 2009, provisional application No. 60/502,498, filed on Sep. 12, 2003, provisional application No. 61/224,938, filed on Jul. 13, 2009, provisional application No. 60/493,935, filed on Aug. 8, 2003, provisional application No. 61/014,814, filed on Dec. 19, 2007, provisional application No. 60/984,786, filed on Nov. 2, 2007.

(56) References Cited

U.S. PATENT DOCUMENTS

| | | |
|---|---|---|
| 3,784,837 A | 1/1974 | Holmstrom |
| RE28,544 E | 9/1975 | Stein et al. |
| 3,961,186 A | 6/1976 | Leunbach |
| 4,047,035 A | 9/1977 | Dennhoven et al. |
| 4,064,440 A | 12/1977 | Roder |
| 4,139,771 A | 2/1979 | Dennhoven et al. |
| 4,210,811 A | 7/1980 | Dennhoven et al. |
| 4,216,499 A | 8/1980 | Kunze et al. |
| 4,366,382 A | 12/1982 | Kotowski |
| 4,380,817 A | 4/1983 | Harding et al. |
| 4,430,568 A | 2/1984 | Yoshida et al. |
| 4,525,854 A | 6/1985 | Molbert et al. |
| 4,566,113 A | 1/1986 | Donges et al. |
| 4,599,740 A | 7/1986 | Cable |
| 4,641,330 A | 2/1987 | Herwig et al. |
| 4,736,401 A | 4/1988 | Donges et al. |
| 4,788,704 A | 11/1988 | Donges et al. |
| 4,799,247 A | 1/1989 | Annis et al. |
| 4,809,312 A | 2/1989 | Annis |
| 4,825,454 A | 4/1989 | Annis et al. |
| 4,864,142 A | 9/1989 | Gomberg |
| 4,870,670 A | 9/1989 | Geus |
| 4,884,289 A | 11/1989 | Glockmann et al. |
| 4,979,202 A | 12/1990 | Siczek et al. |
| 4,991,189 A | 2/1991 | Boomgaarden et al. |
| 5,022,062 A | 6/1991 | Annis |
| 5,065,418 A | 11/1991 | Bermbach et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis et al. |
| 5,313,511 A | 5/1994 | Annis et al. |
| 5,367,552 A | 11/1994 | Peschmann |
| 5,379,334 A | 1/1995 | Zimmer et al. |
| 5,394,454 A | 2/1995 | Harding |
| 5,430,787 A | 7/1995 | Norton |
| 5,493,596 A | 2/1996 | Annis |
| 5,600,303 A | 2/1997 | Husseiny et al. |
| 5,638,420 A | 6/1997 | Armistead |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,692,028 A | 11/1997 | Geus et al. |
| 5,692,029 A | 11/1997 | Husseiny et al. |
| 5,696,806 A | 12/1997 | Grodzins et al. |
| 5,751,837 A | 5/1998 | Watanabe et al. |
| 5,763,886 A | 6/1998 | Schulte |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,974,111 A | 10/1999 | Krug et al. |
| 6,018,562 A | 1/2000 | Willson |
| 6,031,890 A | 2/2000 | Bermbach et al. |
| 6,058,158 A | 5/2000 | Eiler |
| 6,067,344 A | 5/2000 | Grodzins et al. |
| 6,081,580 A | 6/2000 | Grodzins et al. |
| 6,094,472 A | 7/2000 | Smith |
| 6,151,381 A | 11/2000 | Grodzins et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,212,251 B1 | 4/2001 | Tomura et al. |
| 6,218,943 B1 | 4/2001 | Ellenbogen |
| 6,236,709 B1 | 5/2001 | Perry et al. |
| 6,249,567 B1 | 6/2001 | Rothschild et al. |
| 6,252,929 B1 | 6/2001 | Swift et al. |
| 6,256,369 B1 | 7/2001 | Lai |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,320,933 B1 | 11/2001 | Grodzins et al. |
| 6,356,620 B1 | 3/2002 | Rothschild et al. |
| 6,421,420 B1 | 7/2002 | Grodzins |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,453,003 B1 | 9/2002 | Springer et al. |
| 6,453,007 B2 | 9/2002 | Adams et al. |
| 6,456,684 B1 | 9/2002 | Mun et al. |
| 6,459,761 B1 | 10/2002 | Grodzins et al. |

(56) References Cited

U.S. PATENT DOCUMENTS

| | | |
|---|---|---|
| 6,459,764 B1 | 10/2002 | Chalmers |
| 6,473,487 B1 | 10/2002 | Le |
| RE37,899 E | 11/2002 | Grodzins et al. |
| 6,483,894 B2 | 11/2002 | Hartick et al. |
| 6,507,025 B1 | 1/2003 | Verbinski et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,543,599 B2 | 4/2003 | Jasinetzky |
| 6,546,072 B1 | 4/2003 | Chalmers |
| 6,552,346 B2 | 4/2003 | Verbinski et al. |
| 6,556,653 B2 | 4/2003 | Hussein |
| 6,563,903 B2 | 5/2003 | Kang et al. |
| 6,567,496 B1 | 5/2003 | Sychev |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,636,581 B2 | 10/2003 | Sorenson |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,665,433 B2 | 12/2003 | Roder |
| 6,763,635 B1 | 7/2004 | Lowman |
| 6,785,357 B2 | 8/2004 | Bernardi et al. |
| 6,812,426 B1 | 11/2004 | Kotowski et al. |
| 6,816,571 B2 | 11/2004 | Bijjani et al. |
| 6,837,422 B1 | 1/2005 | Meder |
| 6,839,403 B1 | 1/2005 | Kotowski et al. |
| 6,843,599 B2 | 1/2005 | Le et al. |
| 6,876,719 B2 | 4/2005 | Ozaki |
| 6,879,657 B2 | 4/2005 | Hoffman |
| 6,920,197 B2 | 7/2005 | Kang et al. |
| 7,039,159 B2 | 5/2006 | Muenchau et al. |
| 7,099,434 B2 | 8/2006 | Adams et al. |
| 7,103,137 B2 | 9/2006 | Seppi et al. |
| RE39,396 E | 11/2006 | Swift et al. |
| 7,162,005 B2 | 1/2007 | Bjorkholm |
| 7,203,276 B2 | 4/2007 | Arsenault et al. |
| 7,207,713 B2 | 4/2007 | Lowman |
| 7,218,704 B1 | 5/2007 | Adams et al. |
| 7,322,745 B2 | 1/2008 | Agrawal et al. |
| 7,333,587 B2 | 2/2008 | De Man et al. |
| 7,369,463 B1 | 5/2008 | Van Dullemen et al. |
| 7,379,530 B2 | 5/2008 | Hoff et al. |
| 7,400,701 B1 | 7/2008 | Cason |
| 7,486,768 B2 | 2/2009 | Allman et al. |
| 7,505,556 B2 | 3/2009 | Chalmers et al. |
| 7,517,149 B2 | 4/2009 | Agrawal et al. |
| 7,519,148 B2 | 4/2009 | Kotowski et al. |
| 7,551,715 B2 | 6/2009 | Rothschild et al. |
| 7,555,099 B2 | 6/2009 | Rothschild et al. |
| 7,593,506 B2 | 9/2009 | Cason |
| 7,720,195 B2 | 5/2010 | Allman et al. |
| 7,742,568 B2 | 6/2010 | Smith |
| 7,783,004 B2 | 8/2010 | Kotowski et al. |
| 7,809,109 B2 | 10/2010 | Mastronardi et al. |
| 7,817,776 B2 | 10/2010 | Agrawal et al. |
| 7,876,880 B2 | 1/2011 | Kotowski et al. |
| 7,963,695 B2 | 6/2011 | Kotowski et al. |
| 7,995,705 B2 | 8/2011 | Allman et al. |
| 8,000,436 B2 | 8/2011 | Seppi et al. |
| 8,194,822 B2 | 6/2012 | Rothschild et al. |
| 8,275,091 B2 | 9/2012 | Morton et al. |
| 8,503,605 B2 * | 8/2013 | Morton et al. .................. 378/57 |
| 2007/0009088 A1 | 1/2007 | Edic et al. |

FOREIGN PATENT DOCUMENTS

| | | |
|---|---|---|
| EP | 1135700 | 3/2005 |
| EP | 1254384 | 1/2008 |
| EP | 2054741 | 5/2009 |
| EP | 1733213 | 2/2010 |
| EP | 2049888 | 5/2014 |
| GB | 2277013 A | 10/1994 |
| WO | WO9802763 A1 | 1/1998 |
| WO | WO9803889 A1 | 1/1998 |
| WO | WO9820366 A1 | 5/1998 |
| WO | WO9939189 A2 | 8/1999 |
| WO | WO2004010127 A1 | 1/2004 |
| WO | WO2009027667 | 3/2009 |

OTHER PUBLICATIONS

Chou, C., "Fourier coded-aperture imaging in nuclear medicine", IEEE Proc. Sci. Meas. Technol., vol. 141. No. 3, May 1994, pp. 179-184.

European Patent Office Summons to attend oral proceedings pursuant to Rule 115(1) EPC, Application No. 05743513.3-2204/1733213, dated May 6, 2009, 3 pages.

European Patent Office, International Search Report and Written Opinion of the International Searching Authority, PCT/US2005/011382, dated Oct. 21, 2005, 11 pages.

European Patent Office, International Search Report, International Application No. PCT/US99/28266, dated Sep. 6, 2000, 3 pages.

European Patent Office, International Search Report, PCT/US2007/066936; dated: Sep. 30, 2008, 5 pages.

European Patent Office, International Search Report, PCT/US1998/18642, dated Jul. 7, 1999, 6 pages.

European Patent Office, International Search Report, PCT/US1999/028035, dated Sep. 15, 2000, 6 pages.

European Patent Office, Written Opinion of the International Searching Authority, PCT/US2007/066936, dated Sep. 30, 2008, 7 pages.

International Bureau of WIPO, International Preliminary Report on Patentability, PCT/US2005/011382, dated Oct. 19, 2006, 7 pages.

International Preliminary Examining Authority—US, International Preliminary Examination Report, PCT/US1998/018642, dated Aug. 30, 1999, 4 pages.

International Preliminary Examining Authority—US, International Preliminary Examination Report, PCT/US1999/028035, dated Mar. 25, 2002, 3 pages.

International Preliminary Examining Authority—US, Written Opinion, International Application No. PCT/US1999/028035; dated Apr. 20, 2001, 4 pages.

Mertz, L.N., et al, "Rotational aperture synthesis for x rays", Journal. Optical Society of America, vol. 3, Dec. 1966, pp. 2167-2170.

* cited by examiner

FOUR-SIDED IMAGING SYSTEM AND METHOD FOR DETECTION OF CONTRABAND

CROSS REFERENCE

This application relies on U.S. Patent Provisional No. 61/224,938 filed on Jul. 13, 2009 and is hereby incorporated by reference in its entirety.

The present invention is a continuation-in-part of U.S. patent application Ser. No. 12/396,568, entitled "Single Boom Cargo Scanning System", and filed on Mar. 3, 2009, which is a continuation-in-part of U.S. patent application Ser. No. 11/948,814, entitled, "Single Boom Cargo Scanning System", filed on Nov. 30, 2007, and now issued U.S. Pat. No. 7,517,149, which is a continuation of U.S. Pat. No. 7,322,745, entitled, "Single Boom Cargo Scanning System", filed on Aug. 9, 2004, which relies on, for priority, U.S. Provisional Patent Application No. 60/493,935, filed on Aug. 8, 2003 and is a continuation-in-part of U.S. patent application Ser. No. 10/201,543, entitled "Self-Contained Portable Inspection System and Method", filed on Jul. 23, 2002 and now U.S. Pat. No. 6,843,599. The '591 application further relies on U.S. Provisional Application No. 61/014,814, filed on Dec. 19, 2007, for priority.

The present invention is also a continuation-in-part of U.S. patent application Ser. No. 12/395,760, entitled "Single Boon Cargo Scanning System", and filed on Mar. 2, 2009, which is a continuation-in-part of U.S. patent application Ser. No. 12/051,910, entitled "Single Boom Cargo Scanning System", and filed on Mar. 20, 2008, now issued U.S. Pat. No. 7,519,148, which is a continuation of U.S. Pat. No. 7,369,463, of the same title, filed on Jan. 12, 2007, which is a continuation-in-part of U.S. Pat. No. 7,322,745.

The present invention is a continuation-in-part of U.S. patent application Ser. No. 12/339,591, entitled Rotatable Boom Cargo Scanning System, filed on Dec. 19, 2008, which is a continuation-in-part of U.S. patent application Ser. No. 11/948,814, described above and also a continuation-in-part of U.S. patent application Ser. No. 12/051,910, described above.

The present invention is also a continuation-in-part of U.S. patent application Ser. No. 12/753,976, entitled "Self-Contained Mobile Inspection System", and filed on Apr. 5, 2010, which is a continuation-in-part of Ser. No. 12/349,534, of the same title, and filed on Jan. 7, 2009 (and now issued U.S. Pat. No. 7,720,195) which is a continuation of U.S. patent application Ser. No. 10/939,986, entitled "Self-Contained Mobile Inspection System", and filed on Sep. 13, 2004, which is a continuation-in-part of Ser. No. 10/915,687 (issued as U.S. Pat. No. 7,322,745), which is a continuation-in-part of Ser. No. 10/201,543 (issued as U.S. Pat. No. 6,843,599) and further relies on U.S. Provisional Patent Application No. 60/502,498, filed on Sep. 12, 2003, for priority.

The present invention is also a continuation-in-part of U.S. patent application Ser. No. 12/263,160, entitled "Cargo Scanning System", and filed on Oct. 31, 2008, which further relies on U.S. Provisional Patent Application No. 60/984,786, filed on Nov. 2, 2007, for priority, and is a continuation-in-part of U.S. Pat. No. 7,322,745.

The present invention is also a continuation-in-part of U.S. patent application Ser. No. 12/675,471, entitled "Scanning Systems", and filed on Feb. 26, 2010, which is a National Stage Entry of PCT/GB08/02897.

The present invention is also a continuation-in-part of U.S. patent application Ser. No. 12/784,630, entitled "Compact Cargo Mobile Scanning System", and filed on May 21, 2010, which further relies on U.S. Provisional Patent Application No. 61/180,471, of the same title, and filed on May 22, 2009, for priority.

All of the above-listed patent applications are herein incorporated by reference in their entirety.

FIELD OF THE INVENTION

The present invention relates to X-ray scanning and detection systems for screening cars, buses, larger vehicles, and cargo containers for suspicious trade and illicit substances. More specifically, the present invention relates to a four-sided imaging system that provides high detection performance using a combination of transmission and backscatter imaging sensors.

BACKGROUND OF THE INVENTION

X-ray systems are used for medical, industrial and security inspection purposes because they can cost-effectively generate images of internal spaces not visible to the human eye. Materials exposed to X-ray radiation absorb differing amounts of X-ray radiation and, therefore, attenuate an X-ray beam to varying degrees, resulting in a transmitted or back-scattered level of radiation that is characteristic of the material. The attenuated or backscattered radiation can be used to generate a useful depiction of the contents of the irradiated object. A typical single energy X-ray configuration used in security inspection equipment may have a fan-shaped or scanning X-ray beam that is transmitted through or backscattered by the object inspected. The absorption or backscattering of X-rays is measured by detectors after the beam has passed through the object and an image is produced of its contents and presented to an operator.

Trade fraud, smuggling and terrorism have increased the need for such non-intrusive inspection systems in applications ranging from curbside inspection of parked vehicles to scanning in congested or high-traffic ports because transportation systems, which efficiently provide for the movement of commodities across borders, also provide opportunities for the inclusion of contraband items such as weapons, explosives, illicit drugs and precious metals. The term port, while generally accepted as referring to a seaport, also applies to a land border crossing or any port of entry.

With an increase in global commerce, port authorities require additional sea berths and associated container storage space. Additional space requirements are typically met by the introduction of higher container stacks, an expansion of ports along the coastline or by moving inland. However, these scenarios are not typically feasible. Space is generally in substantial demand and short supply. Existing ports operate under a routine that is not easily modified without causing disruption to the entire infrastructure of the port. The introduction of new procedures or technologies often requires a substantial change in existing port operating procedures in order to contribute to the port's throughput, efficiency and operability.

With limited space and a need to expand, finding suitable space to accommodate additional inspection facilities along the normal process route remains difficult. Additionally, selected locations are not necessarily permanent enough for port operators to commit to the long term installation of inspection equipment. Moreover, systems incorporating high-energy X-ray sources, or linear accelerators (LINAC), require either a major investment in shielding material (generally in the form of concrete formations or buildings) or the use of exclusion zones (dead space) around the building itself.

In either case, the building footprint is significant depending upon the size of cargo containers to be inspected.

A mobile inspection system offers an appropriate solution to the need for flexible, enhanced inspection capabilities. Because the system is relocatable and investing in a permanent building in which to accommodate the equipment is obviated, site allocation becomes less of an issue and introducing such a system becomes less disruptive. Also, a mobile X-ray system provides operators, via higher throughput, with the ability to inspect a larger array of cargo, shipments, vehicles, and other containers.

Conventional relocatable inspection systems generally comprise at least two booms, wherein one boom will contain a plurality of detectors and the other boom will contain at least one X-ray source. The detectors and X-ray source work in unison to scan the cargo on the moving vehicle. In conventional single boom relocatable inspection systems, the X-ray source is located on a truck or flatbed and the detectors on a boom structure extending outward from the truck. These systems are characterized by moving-scan-engine systems wherein the source-detector system moves with respect to a stationary object to be inspected. Also, the detectors and the source of radiation are either mounted on a moveable bed, boom or a vehicle such that they are integrally bound with the vehicle. This limits the flexibility of dismantling the entire system for optimum portability and adjustable deployment to accommodate a wide array of different sized cargo, shipments, vehicles, and other containers. As a result these systems can be complicated to deploy and pose several disadvantages and constraints. Conventional systems are disadvantageous in that they suffer from a lack of rigidity, are difficult to implement, and/or have smaller fields of vision.

Accordingly, there is need for improved inspection methods and systems built into a fully self-contained, over-the-road-legal vehicle that can be brought to a site and rapidly deployed for inspection. The improved method and system can, therefore, service multiple inspection sites and set up surprise inspections to thwart contraband traffickers who typically divert smuggling operations from border crossings that have tough interdiction measures to softer crossings with lesser inspection capabilities. Moreover, there is an additional need for methods and systems that require minimal footprint to perform inspection and that use a sufficient range of radiation energy spectrum to encompass safe and effective scanning of light commercial vehicles as well as substantially loaded 20-foot or 40-foot ISO cargo containers. It is important that such scanning is performed without comprising the integrity of the cargo and should ideally be readily deployable in a variety of environments ranging from airports to ports of entry where a single-sided inspection mode needs to be used due to congested environments. Similar needs are addressed in U.S. Pat. No. 6,543,599, entitled "Self-Contained Portable Inspection System and Method", which is herein incorporated by reference in its entirety. In addition, there is a need for improved methods and systems that can provide comprehensive cargo scanning in portable and stationary settings.

Further, in the mobile cargo inspection systems known in the art, the boom structures are typically heavy, thereby causing the overall weight of the scanning system to be close to, or even over the allowable axle load limits. Further, the booms are bulky when stowed such that the vehicle is approximately 4 m high above road level. This makes a mobile scanning system not only difficult to manoeuvre but also restricts its movement in different territories due to the applicable road restrictions on carriage weight. Therefore, there is also a need for a scanning system that can be stowed in a relatively compact area so that it can be easily transported on road, as well as by air. In addition, there is also a need for a scanning system which is light weight, and has a low height and center of gravity in a stowed position, thereby allowing for road transport even in challenging, steep and hilly areas.

Further, inspection typically occurs from only three or fewer directions. For example, a transmission X-ray system will be deployed in a side-shooter or top-shooter configuration while a backscatter system is generally only available in single-sided or three-sided configurations.

Therefore, what is also needed is a four-sided imaging system which provides high detection performance using a combination of transmission and backscatter imaging sensors.

SUMMARY OF THE INVENTION

In one embodiment, the present invention is a scanning system for the inspection of cargo, comprising: a portal defining an inspection area, said portal comprising a first vertical side, a second vertical side, a top horizontal side, and a horizontal base defined by a ramp adapted to be driven over by a vehicle, a first X-ray source disposed on at least one of the first vertical side, second vertical side or top horizontal side for generating an X-ray beam into the inspection area toward the vehicle, a first set of transmission detectors disposed within the portal for receiving the X-rays transmitted through the vehicle, a second X-ray source disposed within the ramp of said portal for generating an X-ray beam towards the underside of the vehicle, and a second set of detectors disposed within the ramp of said portal for receiving X-rays that are backscattered from the vehicle.

In one embodiment, the system is collapsible. In one embodiment, the ramp comprises a base platform hinged to a first angled surface and a second angled surface and wherein, when said system is collapsed, the first angled surface and second angled surface are rotated upward.

In one embodiment, the top horizontal side is connected to said first vertical side at a first end and to said second vertical side at a second end and wherein the first X-ray source is disposed at a point mid way between said first end and said second end.

In one embodiment, the first X-ray source is a high energy source having an energy ranging from 100 kVp to 2 MV. In another embodiment, the second X-ray source is a low energy source having an energy ranging from 60 kVp to 250 kVp.

In one embodiment, the system further comprises a controller, wherein said controller is adapted to activate the first X-ray source only when the second X-ray source is inactive.

In one embodiment, the system further comprises a primary rotating collimator placed adjacent to said first X-ray source, and a secondary static collimator placed adjacent to said rotating collimator and parallel to the inspection surface, wherein said secondary collimator is adapted to generate a first irradiation area in the center of the inspection area and a second irradiation area at a periphery of the inspection area and wherein said second irradiation area is larger than the first irradiation area.

In one embodiment, the system further comprises backscatter detectors in at least one of said first vertical side, said second vertical side, and said top horizontal side. In another embodiment, the backscatter X-ray source is not disposed with said backscatter detectors in at least one of said first vertical side, said second vertical side, and said top horizontal side.

In another embodiment, the present invention is a method for inspecting a vehicle, comprising: providing a portal defining an inspection area, said portal comprising a first vertical side, a second vertical side, a top horizontal side, and a horizontal base defined by a ramp adapted to be driven over by a vehicle; signalling a vehicle to drive over the ramp; irradiating a vehicle with X-rays from a first source disposed on one side of the portal; detecting the X-rays transmitted through the vehicle, using transmission detectors disposed within the portal, to produce a first output signal representative of the vehicle and contents thereof; irradiating the underside of the vehicle with X-rays from a second source disposed within the ramp; detecting X-rays scattered back from the vehicle, using backscatter detectors disposed within the ramp, to produce a second output signal representative of the vehicle and contents thereof; and correlating said first output signal and said second output signal to produce a visual image of the vehicle and contents thereof. In one embodiment, the first X-ray source is operated when said second X-ray source is inactive.

In yet another embodiment, the present invention is a scanning system for inspecting a vehicle, comprising: a portal defining an inspection area, said portal comprising a first vertical side and a second vertical side spaced apart from each other and each having a top side; a third side connecting said two top sides; a ramp over adapted to be driven over by a vehicle; an X-ray source disposed on one side of the portal for generating an X-ray beam into the inspection area; a first set of detectors disposed within the portal for receiving X-rays transmitted through the vehicle; a second set of detectors disposed within the ramp and the first, second and third sides of said portal for receiving X-rays backscattered from the vehicle; and an image processor for receiving output signals from said first and second set of detectors and overlaying said output signals onto a visual image of the vehicle and contents thereof.

In one embodiment, the first set of detectors is disposed on at least two of the same sides of the portal as the second set of detectors. In one embodiment, the first set of detectors comprises a first detector and a second detector adapted to measure an energy component of X-rays transmitted through the vehicle in a range of 0 keV to 50 keV and 20 keV to 200 keV, respectively, and a third detector to measure an energy component of X-rays transmitted through the vehicle in a range of 100 keV to 2 MeV. In one embodiment, the three detectors are in a stacked configuration. In one embodiment, a difference between an output of the third detector and a sum of outputs of the first and second detectors is used to achieve material discrimination.

In one embodiment, the system further comprises a sensor to measure a speed of the vehicle as it passes through the portal. In one embodiment, the system further comprises a controller wherein said controller is in data communication with the sensor and receives the speed of vehicle and wherein said controller is adapted to modulate a pulse rate of the X-ray source to attain a substantially constant dose per unit length of the vehicle under inspection based on the speed.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3a is a schematic representation of one embodiment of a readily collapsible X-ray imaging system in a first configuration;

FIG. 3b illustrates an orthogonal view of one embodiment of a readily collapsible X-ray imaging system in a first configuration, as shown in FIG. 3a;

FIG. 3c is a schematic representation of one embodiment of a readily collapsible X-ray imaging system in a second configuration;

FIG. 3d illustrates an orthogonal view of one embodiment of a readily collapsible X-ray imaging system in a second configuration, as shown in FIG. 3c;

FIG. 3e is a schematic representation of one embodiment of a readily collapsible X-ray imaging system in a third configuration;

FIG. 3f illustrates an orthogonal view of one embodiment of a readily collapsible X-ray imaging system in a third configuration, as shown in FIG. 3e;

DETAILED DESCRIPTION

The present invention is directed towards a four-sided imaging system that provides high detection performance using a combination of transmission and backscatter imaging sensors. The present invention is directed towards multiple embodiments. Language used in this specification should not be interpreted as a general disavowal of any one specific embodiment or used to limit the claims beyond the meaning of the terms used therein. Reference will now be made in detail to specific embodiments of the invention. While the invention will be described in conjunction with specific embodiments, it is not intended to limit the invention to one embodiment.

Figure 1:
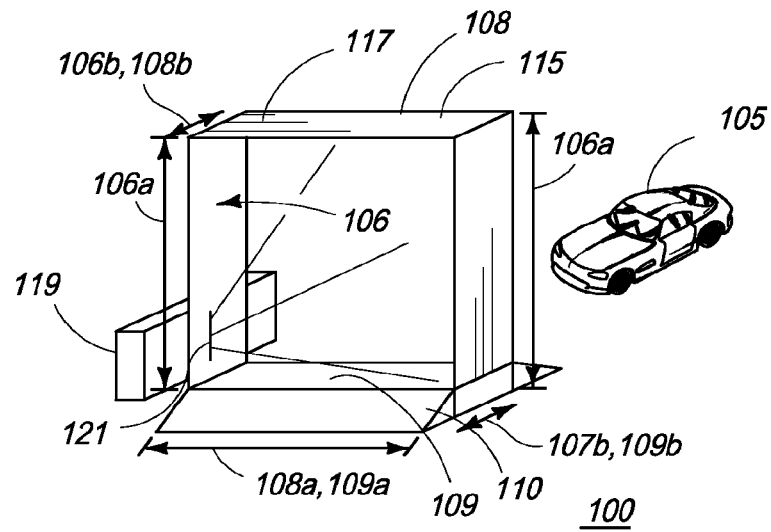
FIG. 1 is a schematic representation of the four-sided X-ray imaging system of the present invention.

FIG. 1 is a schematic representation of one embodiment of a four-sided X-ray imaging system 100. As shown in FIG. 1, vehicle 105 drives over a ramp 110 and underneath an archway 115, which defines an inspection portal. Specifically, the portal is defined by a first (left) side 106, a second (right) side 107, a top side 108 and a bottom platform 109, which is a portion of the ramp. In one embodiment, ramp 110 comprises a base, a first angled surface leading upward to a flat transition point defining the highest part of the ramp, which also functions as the bottom platform 109, and a second angled surface leading back down to the ground. The highest part of the ramp is typically between 50 and 150 mm in height. In one embodiment, archway 115 houses multiple X-ray transmission detectors 117 and at least one X-ray source 119, housed within an enclosure, shown as 220 in FIG. 2.

While FIG. 1 depicts the X-ray source 119 as being on the left side 106 of the portal, one of ordinary skill in the art would appreciate that it could be on the right side 107, with an appropriate reconfiguration of the detectors 117. In one embodiment, the first side 106 has a height 106a in a range of 2 meters to 5 meters and a width 106b in a range of 2 meters to 4 meters; the second side 107 has a height 107a in a range of 2 meters to 5 meters and a width 107b in a range of 2 meters to 4 meters; the top side 108 has a length 108a in a range of 2 meters to 5 meters and a width 108b in a range of 2 meters to 4 meters; and the bottom platform 109 has a length 109a in a range of 2 meters to 5 meters and a width 109b in a range of 2 meters to 4 meters, where the width depends upon the location of the main aperture. Further, bottom platform 109 has a height in a range of 0.2 meter to 0.4 meter, depending upon the width; in one embodiment, a bottom platform 109 having a width of 2 meters has a height of 0.2 meter. Accordingly, the four sides, each having an interior face directed toward the inspection region and an exterior face directed away from the inspection region, define an inspection portal having an inspection area of a minimum of 2 m² to a maximum of 20 m².

Preferably, the enclosure housing the X-ray is physically attached to the exterior face of the first side 106 and is approximately 1 meter tall. The position of the enclosure depends upon the size of the inspection portal. In one embodiment, the enclosure occupies 20% to 50% of the total height of the first side 106. Thus, in one embodiment, if first side 106 is five meters, then the enclosure occupies 20% of the total height. In another embodiment, if first side 106 is 2 meters, the enclosure occupies 50% of the height.

In one embodiment, a slit or opening 121 is provided on first side 106, through which X-rays are emitted. Slit or opening 121 extends substantially up first side 106 to approximately 100% of the height. In one embodiment, slit or opening 121 is covered with a thin coating that is easily transparent to an X-ray. In one embodiment, the thin coating is comprises of a material such as aluminium or plastic and further provides an environmental shield.

In one embodiment, the enclosure and X-ray unit further comprise a first collimator close to the source of X-rays (not shown) and a second collimator close to the exit (not shown), described in greater detail below.

Where the X-ray source enclosure is so positioned, detectors 117 are positioned on the interior face of the second side 107 and the interior face of tope side 108 and occupy the full height of second side 107 and the full length of top side 108, proximate to second side 107.

In another embodiment, the enclosure housing the X-ray is physically attached to the exterior face of the second side 107 and is approximately 1 meter tall. The position of the enclosure depends upon the size of the inspection portal. In one embodiment, the enclosure occupies 20% to 50% of the total height of the first side 107. Thus, in one embodiment, if first side 107 is five meters, then the enclosure occupies 20% of the total height. In another embodiment, if first side 107 is 2 meters, the enclosure occupies 50% of the height. As described above with respect to first side 106, if the enclosure housing the X-ray is on second side 107, a slit or opening (not shown) is similarly provided on second side 107. The detectors are also similarly positioned on the interior faces of top side 108 and first side 106 when the enclosure is on second side 107.

In one embodiment, with a dual-view system, an enclosure housing an X-ray source can be provided on both the first side 106 and second side 107.

Figure 2:
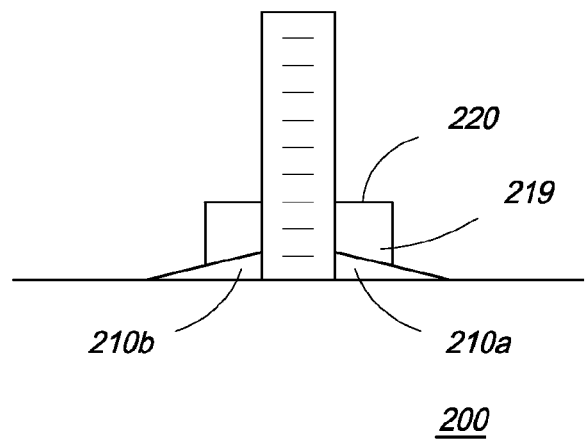
FIG. 2 illustrates an orthogonal view of the four-sided X-ray imaging system of the present invention.

FIG. 2 illustrates an orthogonal view of the system 200, showing both inlet ramp 210a and exit ramp 210b, as well as the X-ray source enclosure 220, containing X-ray source 219.

A transmission system in a "side-shooter" configuration, where the source enclosure is positioned on the first side or second side and emit X-rays toward one side of the vehicle, provides clear inspection of the doors, seats, engine compartment, luggage compartment and roof of the vehicle under inspection. However, such an image provides poor inspection of the floor plan of the vehicle. A "down-shooter" configuration, where the source enclosure is positioned the bottom portion of the first side or second side and emit X-rays from this bottom, lower position in an upward direction, provides a limited inspection capability for the roof of the vehicle since the X-ray signal for this region is superimposed over the complex and more attenuating X-ray signal of the floor (and passengers), thus resulting in an image of marginal value.

In order to provide good penetration of the denser, more highly attenuating objects within the vehicle, such as the engine and luggage compartments, it is advantageous to use a high energy X-ray source, even if tuned to a low output intensity. A suitable high voltage source has an energy ranging from 100 kVp to 2 MV. In one embodiment, at lower energies, a standard X-ray tube source is employed. In another embodiment, at higher energies, a pulse linear accelerator source is employed. In one embodiment of the present invention, standard operating energies are 200 kVp for the lower energy and 1 MV for the higher energy.

Referring back to FIG. 1, in order to provide a high level of inspection capability, ramp 110, over which the vehicle drives is equipped with, and contains therein, a backscatter X-ray unit which comprises a low energy X-ray source, typically having an energy ranging from 60 kVp to 250 kVp, and a plurality of detectors. It should be appreciated that the backscatter unit can be integrated into any floor structure which is movable and deployable to different locations and over which a car can drive. The backscatter signal from the floor of the vehicle is influenced strongly by regions of low atomic number material. Most regions of the vehicle floor are fabricated from high atomic number structural materials such as steel and therefore provide a small backscatter signal. The floor of a car is typically fabricated from relatively thin stamped steel, which typically has a thickness in the range of 1-2 mm. Typically, an X-ray beam can penetrate through this floor and into the objects just above. If low atomic number materials are positioned just above the floor, then these will be visible to X-ray backscatter detectors while they would be invisible to standard visual inspection.

In operating a four-sided imaging system which combines X-ray backscatter with X-ray transmission imaging, it is highly advantageous to use a pulsed accelerator based X-ray source for transmission imaging with a continuous output X-ray source for backscatter imaging since the transmission beam X-ray pulse may be timed to coincide with a period in time when the backscatter system is inactive, thus eliminating any cross-talk between the two X-ray systems and facilitating simultaneous four-sided X-ray inspection. It should also be appreciated that the transmission detectors and backscatter detectors are in data communication with a memory and processor which, in conjunction with a controller, generate one or more transmission and/or backscatter images.

Because it is highly advantageous to be able to rapidly and non-invasively deploy an X-ray system for security screening at a site in order to provide an element of surprise in the screening activity, in one embodiment, the present invention is a rapidly collapsible X-ray system that can be loaded onto a truck for transport between sites.

Figure 3:
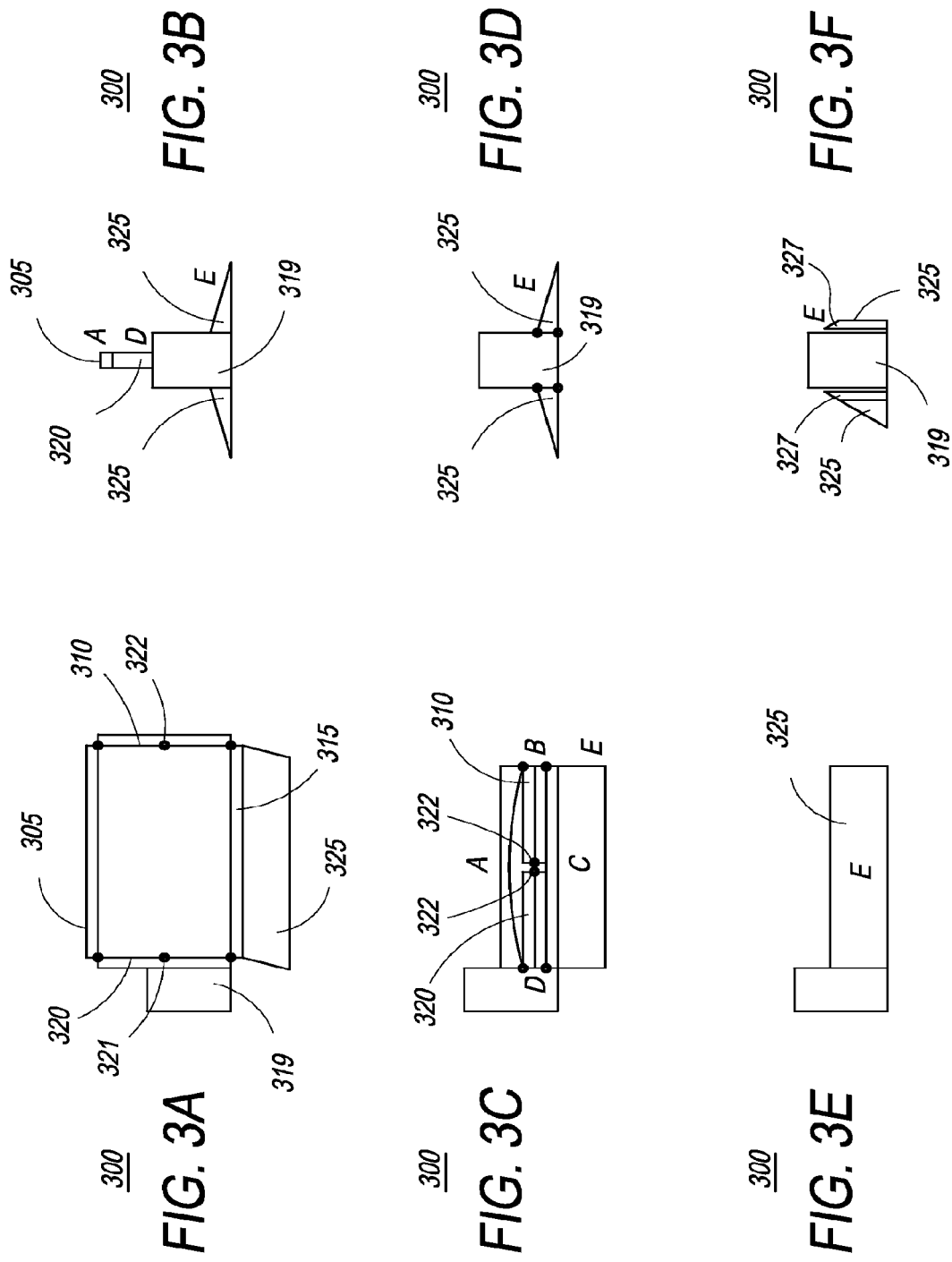

FIGS. 3a, 3b, 3c, 3d, 3e, and 3f depict one embodiment of a rapidly collapsible X-ray imaging system in several configurations. FIG. 3a is a schematic representation of one embodiment of a readily collapsible X-ray imaging system in a first configuration, wherein the system is in a fully deployed position. Rapidly collapsible X-ray imaging system 300 comprises horizontal X-ray sensor section 305, a vertical boom section 310, a drive-over backscatter section 315 and a vertical boom support and collimator section 320 through which the transmission beam propagates from source 319. Further, X-ray imaging system 300 comprises ramp 325 (inlet and outlet) which allows a vehicle to drive over the X-ray backscatter unit seamlessly. FIG. 3b illustrates an orthogonal view of one embodiment of a readily collapsible X-ray imaging system as shown in FIG. 3a. FIG. 3b illustrates source 319, vertical support and collimator section 320, horizontal X-ray sensor section 305, and ramp 325.

The rapidly deployable system of the present invention can be made ready for operation in a period of only a few minutes from arrival at the inspection site. In one embodiment, in order to stow the system ready for transportation, and referring back to FIG. 3a, a set of hydraulic rams or other suitable mechanisms are used to collapse vertical boom sections 310 and 320 inward using hinges 321 and 322, respectively. Hinges 321 and 322 are positioned, in one embodiment, midway up the height of vertical boom sections 310 and 320, respectively. When vertical boom sections 310 and 320 are collapsed inward using hinges 321 and 322, horizontal boom section 305 is "lowered" such that it rests on top of collapsed vertical boom sections 310, 320.

FIG. 3c is a schematic representation of one embodiment of a readily collapsible X-ray imaging system in a second configuration, wherein vertical boom sections 310 and 320 are folded inwards and collapsed at hinges 321, 322. FIG. 3d illustrates an orthogonal view of one embodiment of a readily collapsible X-ray imaging system in a second configuration, as shown in FIG. 3c, further showing ramp 325 and source 319.

FIG. 3e is a schematic representation of one embodiment of a readily collapsible X-ray imaging system in a third configuration, wherein ramp sections 325 are folded upward using hydraulic rams or other suitable mechanisms. FIG. 3f illustrates an orthogonal view of one embodiment of a readily collapsible X-ray imaging system in a third configuration, as shown in FIG. 3e, illustrating ramp 325 which has been folded upwards at both the inlet and outlet. At this point, the system is ready for transport. It should be appreciated that the angled ramp outlet and inlet are hinged to the base platform and capable of moving up such that the tip 327 is directed upward, for achieving system mobility, and moving downward to form the completed ramp. The base platform preferably houses the above-described backscatter system.

In order to deploy the system, the X-ray imaging assembly is placed on site and powered on. Electrical power may be derived from a local mains electricity supply or from an integrated diesel generator. Hydraulic rams or other suitable mechanisms are then used to fold down the two portions (inlet and outlet) of the ramp 325. In one embodiment, the inlet and outlet portions of ramp 325 are folded simultaneously. Once the ramps 325 are down, a second set of hydraulic rams or other suitable mechanisms are used to open vertical boom sections 310 and 320. At this point, the system is ready for use.

In one embodiment, the X-ray imaging system of the present invention is capable of providing an image inspector with information relating to the types of material that are present in the object under inspection. In a large aperture inspection system of this type, a high energy X-ray beam is needed in order to penetrate through the object under inspection. This X-ray beam contains a broad spectrum of X-ray energies ranging from very low energies (typically less than 10 keV) up to the highest energy as determined by the tube or linear accelerator operating voltage (typically in the range of 100 keV to 2 MeV). Due to the unique composition of each material in the object under inspection, the materials each demonstrate specific attenuation of the X-ray beam, wherein this attenuation also comprises an energy dependent component.

Conventionally, a low energy (typically less than 450 kVp) X-ray beam can yield material discrimination information when a thin front detector measures the low energy component of the beam and a thicker rear detector measures the higher energy components of the beam. Here, the two detectors analyze different materials in the object under inspection due to differential photoelectric absorption of the primary X-ray beam. In addition, in the case of a high energy beam (typically in the range 1 MV and above), the fraction of Compton scatter increases markedly. Two relatively thick detectors can be used to discriminate between materials where a first detector is used to absorb the majority of the signal below approximately 200 keV where photoelectric effect dominates while a second detector measures Compton-attenuated signal only.

Figure 4:
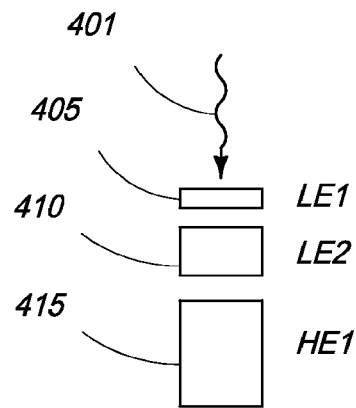
FIG. 4 is an illustration of one embodiment of a triple-stacked detector element.

FIG. 4 is a depiction of a triple-stacked detector. As shown in FIG. 4, incident X-ray beam 401 passes through two low energy detectors, $LE_1$ 405 and $LE_2$ 410, prior to passing through a high energy detector HE 415. Each detector may be formed from a range of X-ray detection materials such as a scintillator (which converts X-ray energy to optical radiation), a semiconductor (which converts X-ray energy to conduction band electrons) or a gas ionization detector (which converts X-ray energy to electron-ion pairs). In one embodiment, the detector configuration described with respect to FIG. 4 is employed with a 1 to 2 MeV system, where the beam energy is above 450 kVp. In one embodiment, first detector $LE_1$ 405 is capable of measuring an energy component of X-rays transmitted through the object in the range of 0 to 50 keV. In one embodiment, second detector $LE_2$ 410 is capable of measuring an energy component of X-rays transmitted through the object in the range of 20 to 200 keV. In one embodiment, third detector HE 415, is capable of measuring an energy component of X-rays transmitted through the object in the range of 100 keV to 2 MeV.

Figure 5:
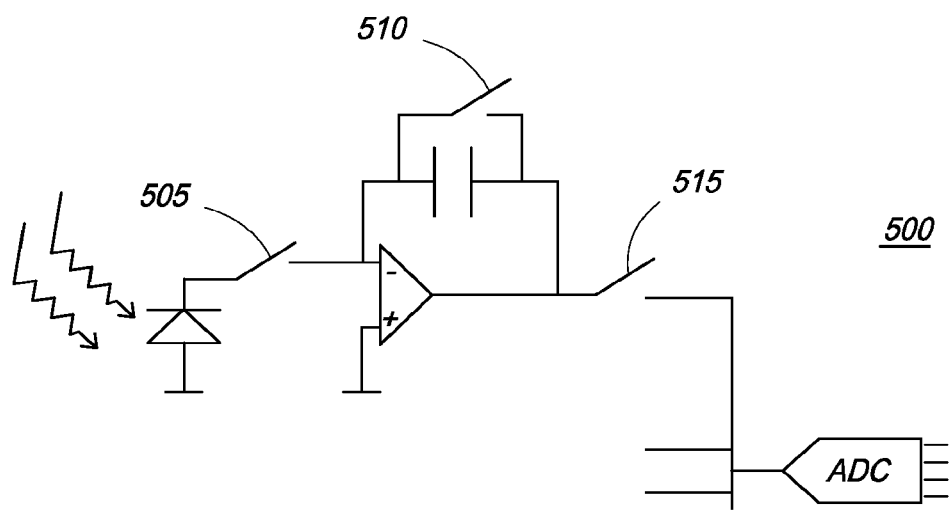
FIG. 5 is an integrator circuit diagram of signal processing as signals from each detector element are passed to the integrator circuits.

In each case, signals from each detector element are passed to integrator circuits, as shown in FIG. 5. In this embodiment, but not limited to such embodiment, a scintillation detector is employed in which an electrical signal generated in a photodiode is converted to a digital value which is directly proportional to the detected X-ray intensity. Independent scintillator/photodiode/integrator circuits are used for each of the three detector elements 405, 410, and 415, shown in FIG. 4.

Referring back to FIG. 5, in operation, integrator 500 is set with switches 505, 510, and 515 in an open position. Just prior to X-ray exposure, switch 505 is closed and integration starts. At the end of the exposure, switch 505 is opened and the stored charge is held on the capacitor. When the analog to digital converter (ADC) is available, switch 515 is closed, and the stored signal is converted to a digital value. At the end of conversion, switch 515 is opened again and switch 510 is closed. This resets the integrator 500 so that it is ready for the next acquisition cycle.

Figure 6A:
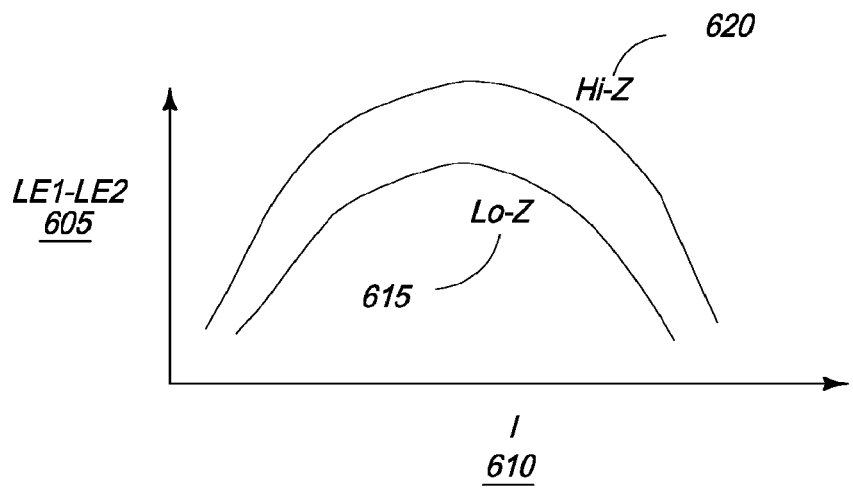
FIG. 6a is a graphical representation of analyzed digital sensor values.
Figure 6B:
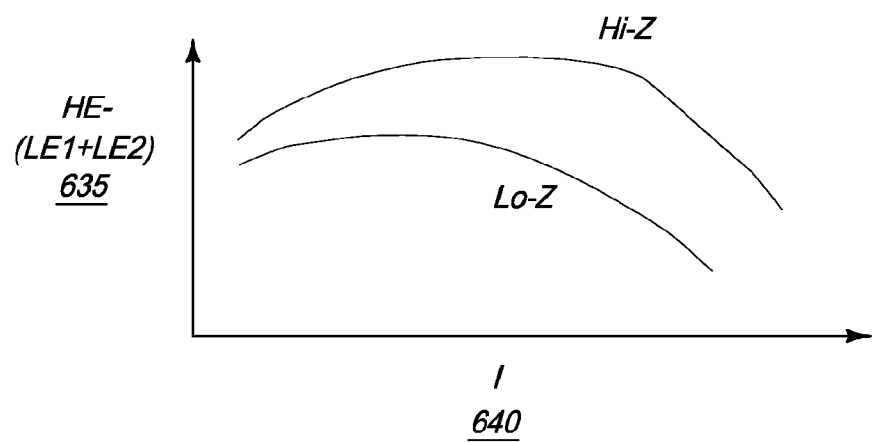
FIG. 6b is another graphical representation of analyzed digital sensor values.

The obtained digital sensor values may then be analyzed, using the above described processor, as shown in FIGS. 6a and 6b. In FIG. 6a, the difference 605 between the two low energy sensors $LE_1$ and $LE_2$, is analyzed as a function of transmitted X-ray beam intensity 610. At both significantly low and significantly high attenuation regions, where there is either no information or where the object is thick and there is no transmission, respectively, the difference between the two sensors is small, but at intermediate intensities, the difference increases to yield material-specific dependence. Two or more thresholds as a function of intensity can be derived to allow materials to be segmented, for example, into organic (Low-Z) and inorganic (High-Z) types, 615 and 620, respectively. Since this method relies on differential absorption of X-rays through the photoelectric effect, the technique does not provide a significant discrimination result at attenuation equivalent to a steel thickness of more than about 20 mm for an energy of about 180 keV or 40 mm for an energy of about 1 MeV.

As shown in FIG. 6b, using the processor to determine the ratio of Compton to photoelectric signals provides materials discrimination over a wider range of object attenuations and is suited to operation at larger material thicknesses. Thus in FIG. 6b, the difference 635 between the high energy sensor HE and the sum of the two low energy sensors $LE_1$ and $LE_2$ [i.e, HE−($LE_1+LE_2$) is analyzed as a function of transmitted X-ray beam intensity 640. Combining the two effects provides a significant improvement over using just two low energy sensors ($LE_1$ and $LE_2$) or a single low energy ($LE_1$ or $LE_2$) and a single high energy (HE) sensor.

Using the separately obtained X-ray backscattering signals, an alternate materials analysis can be performed. Here, the Compton interaction of an X-ray with an electron results in incoherent scattering in which the scattered X-ray has less energy than the incident X-ray. The ability of a material to scatter is dominated by its atomic number (which is roughly proportional to density for solid materials)—the higher the density or atomic number the better it is at scattering. However, dense materials are also very good at absorbing X-rays compared to low density materials. For this reason, low density materials tend to result in a stronger backscattering signal than high density materials. Such a backscatter signal can be used advantageously in a security inspection process.

It should be noted that a signal from an X-ray source falls off as the inverse square of the distance from the source, and thus becomes weaker the farther it is away from the object, with the same effect being true of the scattered radiation from the object. Further, the low energy backscattered signal is strongly absorbed by high density materials such as steel which means that this is a good technique for analysis of the steel floor pan in a car or similar small vehicle where one is interested in locating regions of low density material.

Figure 7:
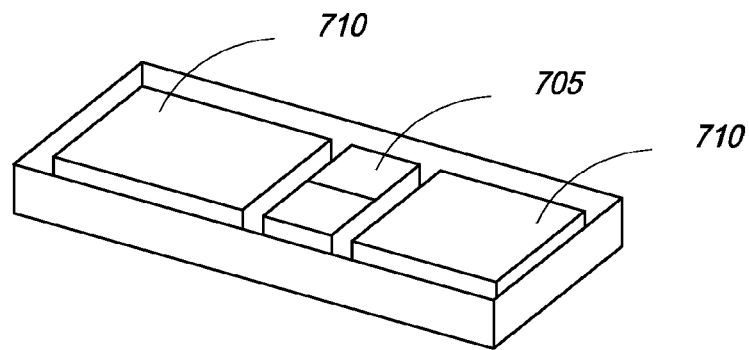
FIG. 7 is an illustration of one embodiment of a sensor that is capable of collecting backscattered radiation information and generating a backscatter image of a region.

FIG. 7 is an illustration of one embodiment of a sensor that is capable of collecting backscattered radiation information and generating a backscatter image of a region. X-ray source 705 generates a thin pencil beam of radiation which, from within the base platform, sweeps rapidly from left to right over the two detector regions 710. The X-ray beam sweeps across the field of view of the object to be inspected typically in a time period of much less than a second and generally ranging from 5 ms to 100 ms. As the beam sweeps across the object under inspection the X-ray backscatter detectors 710 receive scattered signal from the adjacent interaction point of the primary X-ray beam with the object under inspection. The strength of the backscattered signal is dependent on the density at that region of the object. By temporal synchronisation readout of the detector element with the position of the primary beam location, a one-dimensional backscatter image can be obtained. Knowing the speed at which the vehicle moves past the sensor allows a two-dimensional image to be recreated from the set of one-dimensional image sections.

In one embodiment, the detectors are advantageously formed using a large area scintillation detector where the X-ray generated light is reflected into a large area photosensor such as a photomultiplier tube. An alternative embodiment may comprise a gas ionization chamber with a drift field to speed up collection of ion and electron signal currents.

Figure 8:
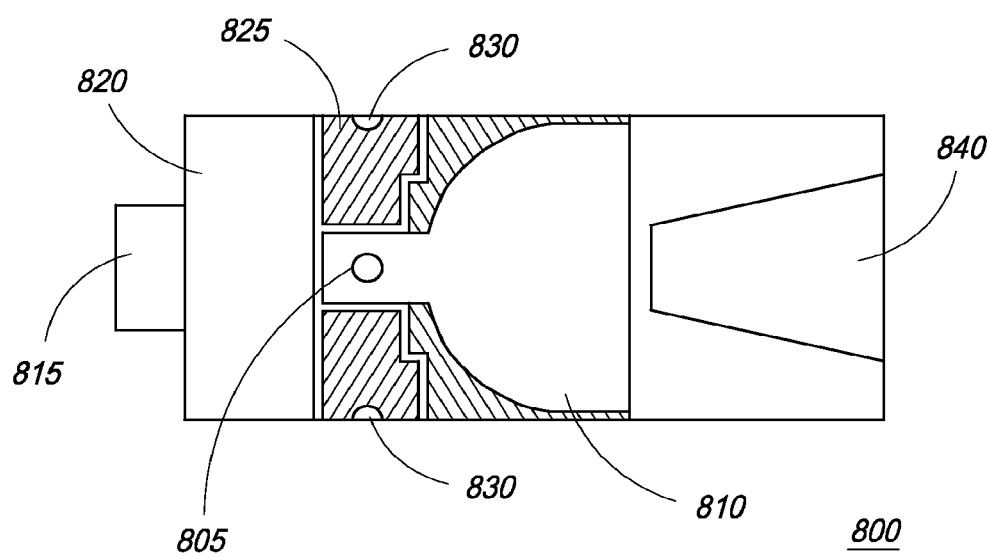
FIG. 8 is a representative cross-section of one embodiment of an X-ray source that may be used with the present invention.

FIG. 8 is a representative cross-section of an X-ray source that may be used with the present invention. Radiation source 800, with an extended anode 805, is shown whereby anode 805 operates at ground potential with a cathode 810 at a negative high voltage. It will be apparent to one skilled in the art that alternative configurations with a grounded cathode and differential systems with a cathode at negative potential and anode at positive potential are also possible. The X-ray source is shielded by suitable materials, such as tungsten and lead, to prevent unwanted radiation from the X-ray tube from reaching the object under inspection.

An electric motor 815 and a gearbox 820 drive a collimator 825 which comprises a solid block of tungsten or a combined tungsten/lead/steel assembly forming one or more predetermined voids, spaces, or holes 830 which allow radiation to be emitted in a pencil-beam fashion in a direction perpendicular to the axis of rotation of the collimator 825. Two such collimator holes 830 are shown diametrically opposed in FIG. 8. A high voltage connection 840 provides a point for electrical connection to the X-ray tube such that the high voltage power supply can be mounted remotely away from the X-ray inspection area.

Figure 9:
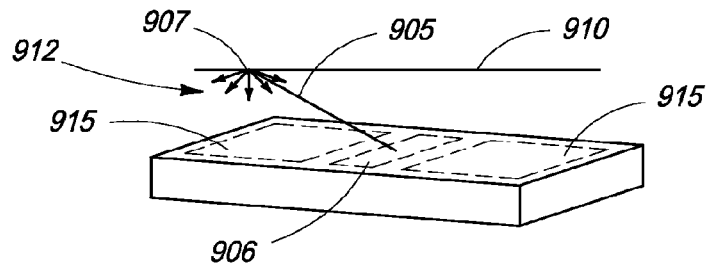
FIG. 9 is an illustration of the X-ray beam as it comes into contact with the object under inspection and the subsequent backscatter.

While in operation, the axis of rotation of the collimator is in the direction of motion of the object under inspection such that the primary X-ray beam sweeps in a direction perpendicular to the motion of the object under inspection. As shown in FIG. 9, the X-ray beam 905 emerges from the source assembly 906 in a first direction and, at the point of intersection 907 of the primary beam 905 with the object to be inspected 910, generates backscattered radiation 912, which interacts with the adjacent X-ray detector 915.

Figure 10A:
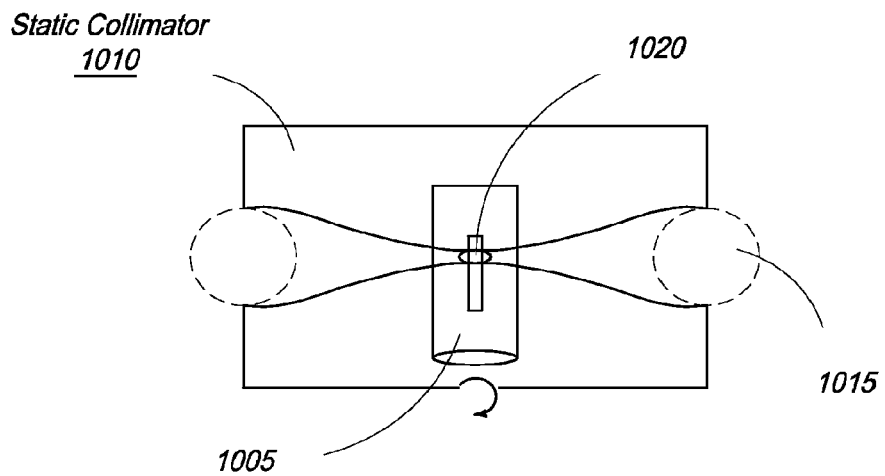
FIG. 10a is an illustration of one embodiment of the present invention in which a pencil-like rotating collimator is replaced with a slot-like rotating collimator.

As described above, the intensity of the primary beam averaged over an area is dependent upon the distance of that measurement point from the source origin. For this reason, the signal received at the periphery of the scanning zone will be less intense than that received nearer to the center of the inspection zone for an identical scattering surface. To address this issue, as shown in FIG. 10a, in one embodiment of the present invention, the pencil-like rotating collimator section is replaced with a slot-like rotating collimator section 1005. A second collimation aperture 1010 is then placed adjacent to the rotating collimator and parallel to the inspection surface. The secondary collimator 1010 is narrow at the center of the inspection area 1015 (directly above the rotating slot collimator 1005) and widens out at distance from the rotating slot collimator. This provides a small irradiation area 1020 in the centre of the inspection region where the primary beam intensity is high and a larger irradiation at the periphery of the inspection region where the primary beam intensity is lower. This preserves the dynamic range of the signal and makes it easier to both collect the data with good signal to noise ratio and to reconstruct the individual scan line object density.

In order to minimize cross talk between the backscatter imaging component and the transmission X-ray imaging system, it is advantageous to synchronize the operation of the two systems. For a rotating backscatter collimator with two apertures, each located substantially opposite to the other (i.e. one rotated at 180 degrees from the other) there are moments in time where neither collimator is emitting a beam onto the object. This occurs with the collimator at both 0 degrees and 180 degrees relative to the scanning plane.

Figure 10B:
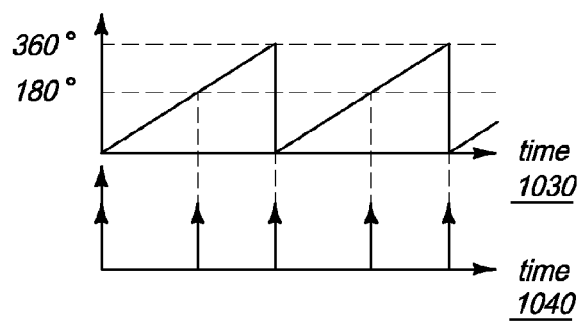
FIG. 10b is a graphical representation of the time at which a pulsed X-ray source can be fired to create a corresponding line of an X-ray transmission image with no interference from the backscatter detector.

Accordingly, As shown in FIG. 10b, it is preferred to activate a pulsed X-ray source at time $T_{1-N}$ 1030 to generate a corresponding line of the transmission X-ray image when the collimator is not emitting a backscatter beam onto the object, shown as times $T'_{1-N}$ 1040, thereby avoiding interference with the backscatter detector. In one embodiment, for an X-ray source pulsing at 100 Hz, the backscatter imaging collimator needs to operate at 50 revolutions per second or 300 RPM. By placing a phase lock loop or equivalent feedback circuit between the collimator motor controller and the X-ray transmission source controller, it is possible to adjust the frequency of the collimator and X-ray source to take into account variation in speed of the object under inspection as it passes through the X-ray imaging system.

Figure 11A:
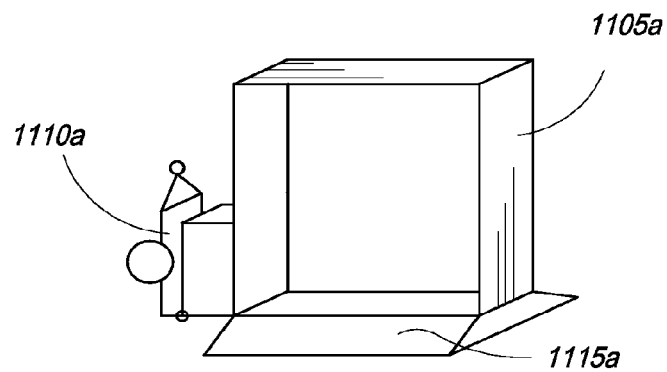
FIG. 11a is an illustration of another embodiment of the present invention in which the scanning assembly may optionally be integrated with a transport trailer, in a first configuration.
Figure 11B:
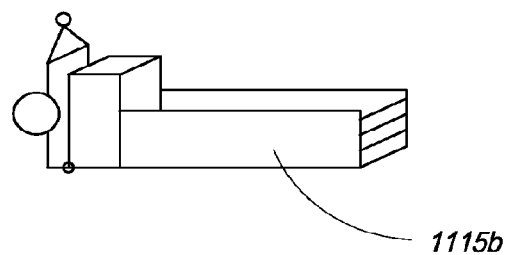
FIG. 11b is an illustration of another embodiment of the present invention in which the scanning assembly may optionally be integrated with a transport trailer, in a second configuration.
Figure 11C:
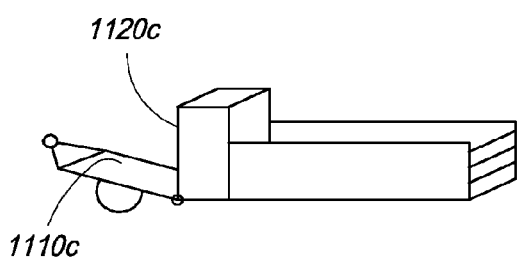
FIG. 11c is an illustration of another embodiment of the present invention in which the scanning assembly may optionally be integrated with a transport trailer, in a third configuration.
Figure 11D:
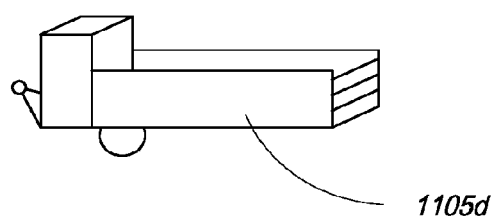
FIG. 11d is an illustration of another embodiment of the present invention in which the scanning assembly may optionally be integrated with a transport trailer, in a fourth configuration.

As shown in FIGS. 11a, 11b, 11c, and 11d, in another embodiment of the present invention, the mechanical scanning assembly may optionally be integrated with a trailer to permit towing of the equipment behind a vehicle. FIG. 11a shows system 1105a in a first configuration, deployed and ready for use where the transport trailer 1110a is folded up at the side of the inspection system and vehicle ramps 1115a are in an open and ready to be drive-over position. When it is time to stow the equipment, the detector arrays are folded down and the vehicle ramps 1115b are folded up, as shown in FIG. 11b such that the system is in a second configuration. As shown in FIG. 11c, in a third configuration, the trailer 1110c is lowered, lifting up one end of the imaging equipment 1120c. As shown in FIG. 11d, a winch or other mechanism is then used to pull the X-ray system 1105d onto the trailer ready for transport, in a fourth configuration. To deploy the system, the above described process is implemented in reverse. Advantageously, the vehicle which is used to tow the trailer is provided with image inspection computers, which one or more operators can use to analyze images and so divert and stop vehicles for further search as required and which comprises the aforementioned memory and processors used to process incoming backscatter and transmission data signals.

Figure 12:
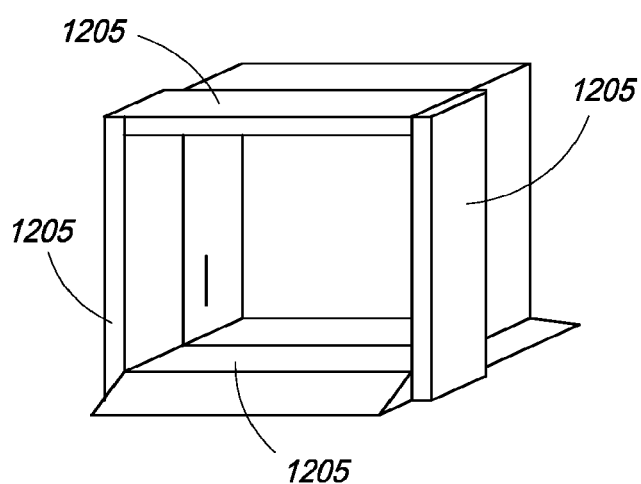
FIG. 12 depicts another embodiment of the present invention in which a four-sided backscatter detector is mounted around the periphery of the scanning volume/tunnel.

FIG. 12 depicts another embodiment of the present invention in which a four-sided backscatter detector 1205 is mounted around the periphery of the scanning tunnel. Each panel of the detector is similar to the sensor described with reference to FIGS. 7, 8, 9, and 10a, but now a four-sided backscatter image may also be generated. Advantageously, the backscatter detectors are mounted to the same frame as the transmission X-ray system such that simultaneous transmission and backscatter image data can be acquired. This allows overlay of backscatter and transmission X-ray images by suitable image manipulation. In this embodiment, backscatter detectors, and not a backscatter X-ray source, are integrated into one or more of the first side 106, second side 107, and top side 108. Alternatively, backscatter detectors, and not a backscatter X-ray source, may be integrated into all three of the first side 106, second side 107, and top side 108. Alternatively, backscatter detectors with a backscatter X-ray source may be integrated into one or more of the first side 106, second side 107, and top side 108.

Figure 13A:
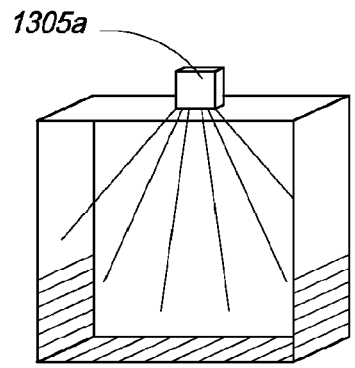
FIG. 13a depicts another embodiment of the X-ray system of the present invention with an alternate transmission X-ray imaging geometry.
Figure 13B:
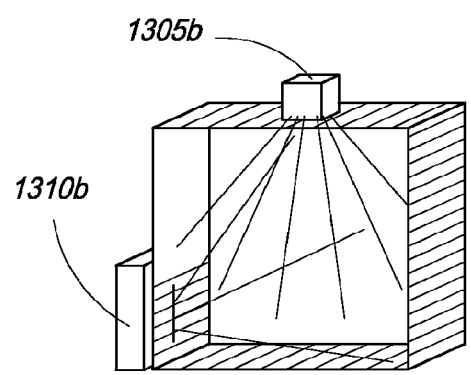
FIG. 13b depicts another embodiment of the X-ray system of the present invention with an alternate transmission X-ray imaging geometry.
Figure 13C:
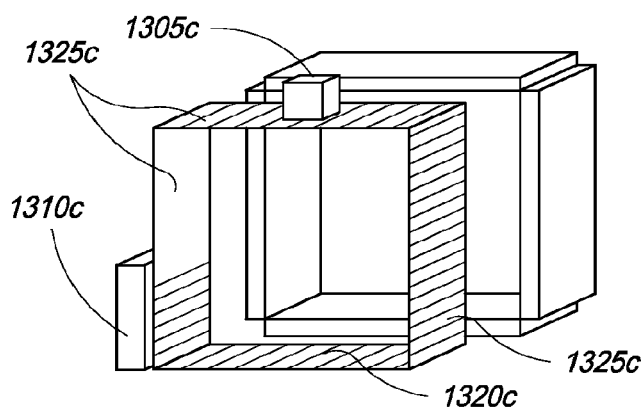
FIG. 13c depicts another embodiment of the X-ray system of the present invention with an alternate transmission X-ray imaging geometry.

FIGS. 13a, 13b, and 13c depict other embodiments of the X-ray system of the present invention with alternate transmission X-ray imaging geometries. FIG. 13a shows the X-ray source 1305a in a "down-shooter" configuration, while FIG. 13b shows a combination or dual-view system that includes both "down-shooter" 1305b and "side-shooter" 1310b. FIG. 13c shows a dual-view system, with both down-shooter 1305c and side-shooter 1310c, further comprising a four-sided backscatter system, with a backscatter source and backscatter detectors integrated into the base of the system 1320c and backscatter detectors, together with transmission detectors, integrated into each of the remaining three sides 1325c. It should be evident to those of ordinary skill in the art that other configurations can be derived based on this disclosure.

Figure 14:
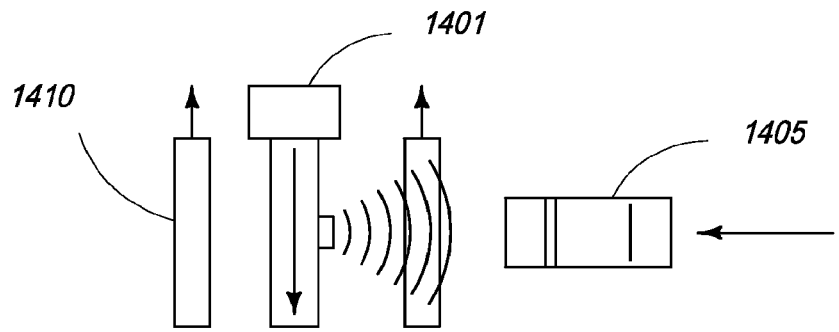
FIG. 14 is an illustration on another embodiment of the present invention where the system further includes vehicle detect sensors.

FIG. 14 is an illustration of one embodiment of the present invention where the system further comprises at least one, and preferably a combination of two, vehicle presence detection sensors 1405 and 1410, to the right and left, respectively, of the main gantry 1401. Sensor 1405 is used to turn the X-ray beam on when the vehicle approaches. This is the right-most sensor when the vehicle approaches from the right as shown in the diagram. Sensor 1410 (the left most sensor in the diagram) is used to turn the X-ray beam off once the vehicle has passed through the imaging plane. In one embodiment, an additional sensor may be used to measure the speed of the vehicle as it passes through the sensor. Vehicle speed may be used to modulate the speed of collimator rotation and source pulse rate to ensure that good image quality is maintained independent of vehicle speed. This also allows a constant dose per unit length of the vehicle under inspection to be delivered which helps to ensure a known and safe dose to the driver and other occupants of the vehicle during X-ray screening.

Figure 15:
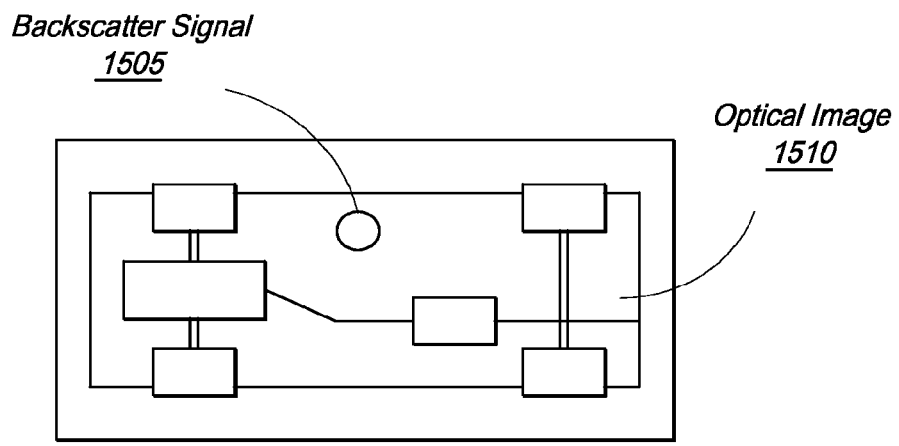
FIG. 15 is a composite image which overlays a backscatter signal with an optical image.

FIG. 15 shows a composite image which overlays the X-ray backscatter signal 1505 from the underside of the vehicle under inspection to be correlated with an optical image 1510 of the same vehicle that is acquired using a suitable optical system at the same time the X-ray image is acquired.

Figure 16:
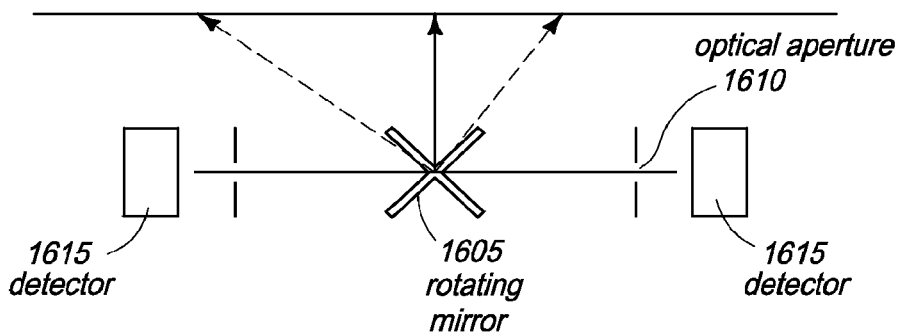
FIG. 16 depicts an exemplary mechanism by which the optical image can be generated by taking an image signal from a mirror.

FIG. 16 shows an exemplary mechanism by which the optical image can be generated by taking an image signal from a mirror 1605 which rotates with the X-ray collimator through one or more optical filters 1610 to one or more photo detectors 1615. This configuration ensures the optical image is captured at a known time relative to the generation of a transmission image.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A scanning system for the inspection of cargo, comprising:
   a portal defining an inspection area, said portal comprising a first vertical side, a second vertical side, a top horizontal side, and a horizontal base defined by a ramp adapted to be driven over by a vehicle;
   a first X-ray source disposed on at least one of the first vertical side, second vertical side or top horizontal side for generating an X-ray beam into the inspection area toward the vehicle;
   a first set of transmission detectors disposed within the portal for receiving the X-rays transmitted through the vehicle;
   a second X-ray source disposed within the ramp of said portal for generating an X-ray beam towards an underside of the vehicle; and
   a second set of detectors disposed within the ramp of said portal for receiving X-rays that are backscattered from the vehicle.

2. The system of claim 1, wherein said first X-ray source is a high energy source having an energy ranging from 100 kVp to 2 MV.

3. The system of claim 1, wherein said second X-ray source is a low energy source having an energy ranging from 60 kVp to 250 kVp.

4. The system of claim 1, further comprising a controller, wherein said controller is adapted to activate the first X-ray source only when the second X-ray source is inactive.

5. The system of claim 1, wherein said system is collapsible.

6. The system of claim 5, wherein said ramp comprises a base platform hinged to a first angled surface and a second angled surface and wherein, when said system is collapsed, the first angled surface and second angled surface are rotated upward.

7. The system of claim 1, wherein said top horizontal side is connected to said first vertical side at a first end and to said second vertical side at a second end and wherein the first X-ray source is disposed at a point mid-way between said first end and said second end.

8. The system of claim 1 further comprising a primary rotating collimator placed adjacent to said first X-ray source, and a secondary static collimator placed adjacent to said rotating collimator and parallel to the inspection surface, wherein said secondary collimator is adapted to generate a first irradiation area in the center of the inspection area and a second irradiation area at a periphery of the inspection area and wherein said second irradiation area is larger than the first irradiation area.

9. The system of claim 1 further comprising backscatter detectors in at least one of said first vertical side, said second vertical side, and said top horizontal side.

10. The system of claim 9 wherein a backscatter X-ray source is not disposed with said backscatter detectors in at least one of said first vertical side, said second vertical side, and said top horizontal side.

11. A method for inspecting a vehicle, comprising:
   providing a portal defining an inspection area, said portal comprising a first vertical side, a second vertical side, a top horizontal side, and a horizontal base defined by a ramp adapted to be driven over by a vehicle;
   irradiating a vehicle with X-rays from a first source disposed on one side of the portal;
   detecting the X-rays transmitted through the vehicle, using transmission detectors disposed within the portal, to produce a first output signal representative of the vehicle and contents thereof;
   irradiating an underside of the vehicle with X-rays from a second source disposed within the ramp;
   detecting X-rays scattered back from the vehicle, using backscatter detectors disposed within the ramp, to produce a second output signal representative of the vehicle and contents thereof; and
   correlating said first output signal and said second output signal to produce a visual image of the vehicle and contents thereof.

12. The method of claim 11, wherein said first X-ray source is a high energy source having an energy ranging from 100 kVp to 2 MV.

13. The method of claim 11, wherein said second X-ray source is a low energy source having an energy ranging from 60 kVp to 250 kVp.

14. The method of claim 11, wherein said first X-ray source is operated when said second X-ray source is inactive.

15. A scanning system for inspecting a vehicle, comprising:
   a portal defining an inspection area, said portal comprising a first vertical side and a second vertical side spaced apart from each other and each having a top side;
   a third side connecting said two top sides;
   a ramp adapted to be driven over by a vehicle;
   an X-ray source disposed on one side of the portal for generating an X-ray beam into the inspection area;
   a first set of detectors disposed within the portal for receiving X-rays transmitted through the vehicle;
   a second set of detectors disposed within the ramp and at least two of the first, second and third sides of said portal for receiving X-rays backscattered from the vehicle; and
   an image processor for receiving output signals from said first and second set of detectors and overlaying said output signals onto a visual image of the vehicle and contents thereof.

16. The system of claim 15, wherein said first set of detectors is disposed on at least two of the same sides of the portal as the second set of detectors.

17. The system of claim 15, wherein said first set of detectors comprises a first detector and a second detector adapted to measure an energy component of X-rays transmitted through the vehicle in a range of 0 keV to 50 keV and 20 keV to 200 keV, respectively, and a third detector to measure an energy component of X-rays transmitted through the vehicle in a range of 100 keV to 2 MeV.

18. The system of claim 17, wherein said three detectors are in a stacked configuration.

19. The system of claim 17, wherein a difference between an output of the third detector and a sum of outputs of the first and second detectors is used to achieve material discrimination.

20. The system of claim 15 further comprising a sensor to measure a speed of the vehicle as it passes through the portal.

21. The system of claim 20, further comprising a controller wherein said controller is in data communication with the sensor and receives the speed of vehicle and wherein said controller is adapted to modulate a pulse rate of the X-ray source to attain a substantially constant dose per unit length of the vehicle under inspection based on the speed.

* * * * *